United States Patent [19]

Sciavolino

[11] 4,283,527

[45] Aug. 11, 1981

[54] ERYTHROMYCYLAMINE 11,12-CARBONATE AND DERIVATIVES THEREOF

[75] Inventor: Frank C. Sciavolino, East Lyme, Conn.

[73] Assignee: Pfizer Inc., New York, N.Y.

[21] Appl. No.: 136,197

[22] Filed: Apr. 1, 1980

[51] Int. Cl.³ .......................................... C07H 17/08
[52] U.S. Cl. ........................................ 536/9; 424/180
[58] Field of Search ............................................ 536/9

[56] References Cited

U.S. PATENT DOCUMENTS

| | | | |
|---|---|---|---|
| 3,417,077 | 12/1968 | Murphy et al. | 536/9 |
| 4,150,220 | 4/1979 | Sciavolino | 536/9 |

OTHER PUBLICATIONS

Wildsmith, "Tetrahedron Letters", 1972, No. 1, pp. 29–30.
Dziegielewska et al., "Polish Jour. of Chemistry", vol. 53, No. 12, pp. 2551–2554, 1979.

*Primary Examiner*—Johnnie R. Brown
*Attorney, Agent, or Firm*—Francis X. Murphy; Charles J. Knuth; Albert E. Frost

[57] ABSTRACT

Erythromycylamine 11,12-carbonate, its 2'-acetyl-, 2'-propionyl- and 2'-(3-carbethoxypropionyl)-derivatives; N-(carbobenzoxy)-derivatives and pharmaceutically acceptable acid addition salts of said compounds; their use as antibacterial agents; and processes for their preparation.

11 Claims, No Drawings

ERYTHROMYCYLAMINE 11,12-CARBONATE AND DERIVATIVES THEREOF

BACKGROUND OF THE INVENTION

This invention relates to semisynthetic macrolides, and more particularly to erythromycylamine 11,12-carbonate, its 2'-acetyl-, 2'-propionyl- and 2'-(3-carbethoxypropionyl)- derivatives; to pharmaceutically acceptable acid addition salts thereof; and to methods for their preparation and use as antibacterial agents. Erythromycin A is a macrolide antibiotic produced by fermentation and described in U.S. Pat. No. 2,653,899. Numerous derivatives of erythromycin A have been prepared in efforts to modify its biological and/or pharmacodynamic properties.

Erythromycin A esters with mono- and dicarboxylic acids are reported in Antibiotics Annual, 1953–1954, Proc. Symposium Antibiotics (Washington, D.C.), pages 500–513 and 514–521, respectively. U.S. Pat. No. 3,417,077 describes the cyclic carbonate ester of erythromycin A, the reaction product of erythromycin A and ethylene carbonate, as an active antibacterial agent.

The 9-amino derivative of erythromycin A, known as erythromycylamine, has been extensively investigated and derivatized. Sulfonamide derivatives of erythromycylamine are described in U.S. Pat. No. 3,983,103 as antibacterial agents. N-substituted derivatives of erythromycylamine are reported by Ryden et al., J. Med. Chem., 16, 1059 (1973), and by Witzel, et al., in U.S. Pat. No. 4,016,263 as antibacterial agents for oral or parenteral use. Various aldehyde-erythromycylamine condensation products are described in U.S. Pat. Nos. 3,681,322 and 4,048,306 and Belgian Pat. No. 840,431 as antibacterial agents.

Methods for preparing 9(S)- and 9(R-)-erythromycylamines are described by Massey et al., in Tetrahedron Letters, 157 (1970); Wildsmith, Tetrahedron Letters, 29 (1972); and Massey et al., J. Med. Chem., 17 105–107 (1974).

SUMMARY OF THE INVENTION

It has now been found that erythromycylamine 11,12-carbonate, the cyclic carbonate ester of erythromycylamine, its 2'-acetyl-, 2'-propionyl- and 2'-(3-carbethoxypropionyl)-derivatives are effective anti-bacterial agents via the oral and parenteral routes of administration, particularly against Gram-positive microorganisms. Also valuable for the same purpose are the pharmaceutically acceptable acid addition salts of said compounds.

Included in this invention are the cyclic carbonate esters of the 9(R)- and the 9(S)-epimers of erythromycylamine, and intermediates therefor. The formula presented below is generic to and embracive of both of said epimeric forms:

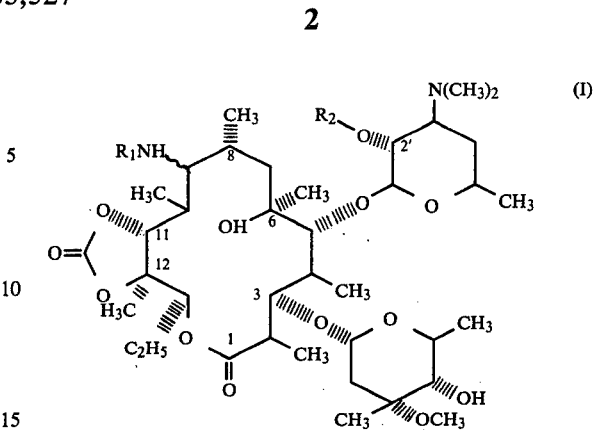

wherein $R_1$ is hydrogen or carbobenzoxy; and $R_2$ is hydrogen, acetyl, propionyl or 3-carbethoxypropionyl.

Principal interest resides in the cyclic carbonate ester of the erythromycylamine epimer prepared by the procedure of Wildsmith, Tetrahedron Letters, 29 (1972) and which is identified as the 9(S)-epimer. Compounds of formula I derived from the 9(S)-epimer generally exhibit greater antibacterial properties relative to those of the 9(R)-epimer.

Compounds of the above formula wherein $R_1$ is hydrogen and pharmaceutically acceptable acid addition salts thereof are effective antibacterial agents against Gram-positive microorganisms, e.g. *Staphylococcus aureus* and *Streptococcus pyogenes*, in vitro and in vivo via the parenteral and oral routes of administration and also against certain Gram-negative microorganisms, such as cocci, e.g., *Pasteurella multocida* and *Neisseria sicca*.

DETAILED DESCRIPTION OF THE INVENTION

Erythromycylamine 11,12-carbonate and its 2'-acyl derivatives are prepared according to the following reaction sequence wherein E represents the moiety

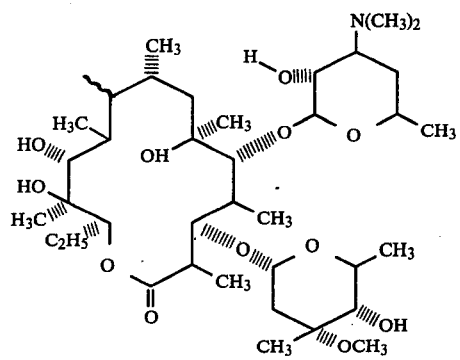

and Cbz represents the carbobenzoxy group $C_6H_5—CH_2—O—CO—$.

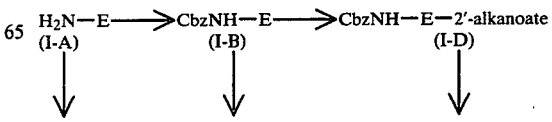

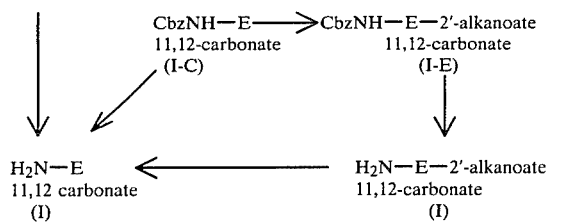

*In this sequence, alkanoate includes 3-carbethoxypropionyl; propionyl and acetyl.

The conversion of erythromycylamine (I-A) to the carbobenzoxy derivative (I-B) is accomplished by acylation of erythromycylamine with carbobenzoxy chloride in a suitable reaction medium in the presence of an acid acceptor. The acylation can be conducted in aqueous or non-aqueous solvent systems. In aqueous systems, the reaction is generally carried out at a pH of from about 6 to 9 and at a temperature of from about 0° C. to about 50° C. It can also be performed in unstable emulsions of water and water-immiscible organic solvents such as methyl isobutyl ketone and lower alkyl acetates over the pH range from about 2 to about 4. In non-aqueous systems the reaction is also carried out at from about 0° C. to about 50° C. in the presence of an acid acceptor.

Suitable acid acceptors are tertiary amines such as trialkylamines having from 1 to 4 carbon atoms per alkyl group, N-methylaniline, pyridine, N-ethylpyridine and N-methylmorpholine. When an aqueous reaction medium is used, an inorganic base such as an alkali metal hydroxide or bicarbonate can be used as acid acceptor.

The molar ratio of erythromycylamine:carbobenzoxy chloride:acid acceptor can vary from 1:1:1 to 1:1.2:1.5. It is generally desirable to use an excess of carbobenzoxychloride to expedite the reaction and to insure optimum acylation of the erythromycylamine. The molar amount of acid acceptor used should be at least equal to the molar amount of carbobenzoxy chloride used. In practice an excess of acid acceptor over that requested in the basis of the amount of carbobenzoxy chloride used is generally employed to expedite the reaction. However, beyond the requirement that about molar proportions of reactants be used, there is nothing critical regarding the excesses of carbobenzoxy chloride and acceptor used, except, of course the need that the molar proportion of acid acceptor be at least equal to the carbobenzoxy chloride used.

The acylated product is recovered by methods known in the art.

In addition to the carbobenzoxy group, which serves as "protecting" group, other known nitrogen protecting groups, such as trifluoroacetyl-, t-butyloxycarbonyl- and 2,2,2-trichloroethoxy carbonyl which are removable under mild conditions can be used. Such groups are attached to the 9-amino group by known procedures and are subsequently removed by standard procedures, such as hydrolysis.

The carbobenzoxylated derivative (I-B) is acylated with an appropriate acylating agent according to methods known to those skilled in the art to produce the 2'-alkanoyl (acetyl, propionyl), 3-carbethoxypropionyl) derivative (I-D). Suitable acylating agents are the appropriate acid chloride, and acid anhydrides (simple or mixed). The reaction is conducted in a reaction-inert solvent such as ethyl acetate, dioxane, tetrahydrofuran, methylene chloride and acetone.

When an acid chloride is used as acylating agent addition of an acid acceptor is not necessary since the erythromycylamine moiety (E) contains a basic dimethylamino group which serves as acid acceptor.

Additionally, the acylation can be accomplished by using the appropriate acid in the presence of a condensing agent such as carbodiimide according to known procedures.

When using a carbodiimide as condensing agent, aqueous or non-aqueous solvent systems can be used. When an aqueous system is used, pH is desirably adjusted to the range of about 5 to about 8, and preferably to about 6 to about 7. In a typical procedure, the acid reactant and carbodiimide are mixed in equimolar proportions in a suitable solvent (tetrahydrofuran, dioxane), and a solution of water and a water miscible organic solvent (water plus dioxane or tetrahydrofuran) containing the formula I-B reactant is added at room temperature. The mixture is stirred for several hours until reaction is complete. Temperatures of from about $-5°$ C. to about 30° C. are generally used. In most instances, an excess of up to about 10% of the condensing agent is used. The acylated product is recovered by methods known in the art.

The 11,12-carbonate derivative (I-C) of carbobenzoxylated erythromycylamine (I-B) is produced by reacting I-B with an alkylene carbonate in a reaction-inert solvent medium. Suitable solvents are hydrocarbon solvents such as benzene, xylene and toluene, tetrahydrofuran, dioxane, ether, diethylene glycol dimethyl ether and ethyl acetate.

The reaction is conducted in the presence of a base as catalyst. Organic and inorganic bases such as tertiary amines (tri-$C_{1-4}$ alkyl)amines, triethanolamine, N-methyl morpholine, basic resins; sodium or potassium carbonate, bicarbonate and hydroxide are useful. Anhydrous potassium carbonate is favored because it affords satisfactory yields of desired product of high quality. Other alkali metal salts such as cyanides, chlorides, cyanates, bromides, iodides and thiocyanates also serve as catalysts in this esterification process.

By means of the above procedure, the carbobenzoxylated 11,12-carbonate derivative (I-C) is acylated to the corresponding 2'-alkanoyl derivative (I-E).

The preferred alkylene carbonate is ethylene carbonate because of its ready availability. However, other alkylene carbonates consisting of 5- to 7-membered rings and which are unsubstituted or substituted with, for example, methyl or other alkyl groups can be used. Representative of such alkylene carbonates are 4,4-dimethyl-1,3-dioxolan-2-one; 4-methyl-1,3-dioxolan-2-one; 4,5-dimethyl-1,3-dioxolan-2-one; 1,3-dioxan-2-one; 4-methyl-1,3-dioxan-2-one; and 1,3-dioxapan-2-one.

The amount of alkylene carbonate used is not critical but it is desirable to use an excess of alkylene carbonate in order to obtain satisfactory yields. From five to ten moles of alkylene carbonate per mole of the erythromycylamine compound or derivative thereof are generally favored.

The reaction is carried out at a temperature of from about 70° C. to about 120° C. Lower temperatures can be used, as for example would be the case when ether is used as solvent, but are generally avoided because of the much longer reaction periods required. The 11,12-carbonate I-C is recovered by procedures known to those skilled in the art.

In like manner, the carbobenzoxylated 2'-alkanoyl derivative (I-D) is converted to the 11,12-carbonate derivative (I-E). Removal of the carbobenzoxy group from I-C by catalytic hydrogenation over, for example, palladium-on-carbon affords the corresponding 11,12-carbonates of 2'alkanoyl erythromycylamine (I, R=alkanoyl) and erythromycylamine (I, R=H), respectively, The catalytic reduction is conducted according to known procedures for removal of the protective carbobenzoxy group.

A favored procedure for preparing erythromycylamine 11,12-carbonate (I, R=H) comprises direct esterification of erythromycylamine (I) using an alkylene carbonate in the presence of a catalyst according to the procedure described above. The desired product is isolated by taking advantage of its basic nature. An aqueous solution of the crude product is extracted over a range of gradually increasing pH such that neutral or non-basic materials are extracted at lower pH's and the product at a pH of about 10. The extracting solvents, ethyl acetate, or diethyl ether or methylene chloride are back washed with brine and water, dried over sodium sulfate, and evaporated to provide the product.

Acid addition salts of the compounds of this invention are readily prepared by treating compounds having formula I with at least an equimolar amount of the appropriate acid in a reaction-inert solvent. When more than one basic group is present in a compound of formula I, the addition of sufficient acid to satisfy each basic group permits formation of polyacid addition salts. The acid addition salts are recovered by filtration if they are insoluble in the reaction-inert solvent, by precipitation by addition of a non-solvent for the acid addition salt, or by evaporation of the solvent. Representative of such salts, but not limited thereto, are the hydrochloride, hydrobromide, phosphate, sulfate, formate, acetate, propionate, butyrate, citrate, glycolate, lactate, tartrate, malate, maleate, fumarate, gluconate, stearate, mandelate, pamoate, benzoate, succinate, lactate, p-toluenesulfonate and aspartate. When preparing acid addition salts of formula I compounds wherein $R_2$ is alkanoyl, isopropanol is used as solvent to avoid solvolysis of the alkanoyl group.

Compounds of formula I herein exhibit in vitro activity against a variety of Gram-positive microorganisms and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like, for sterilization purposes, e.g. sick-room utensils; and as industrial antimicrobials, for example, in water treatment, slime control, paint and wood preservation.

For in vitro use, e.g. for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent up to about 10 percent by weight based on total composition.

Additionally, many compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for 4 days after the last treatment and the number of survivors is noted.

When used in vivo, these novel compounds can be administered orally or parenterally, e.g. by subcutaneous or intramuscular injection, at a dosage of from about 1 mg./kg. to about 200 mg./kg. of body weight per day. The favored dosage range is from about 5 mg./kg. to about 100 mg./kg. of body weight per day and the preferred range from about 5 mg./kg. to about 50 mg./kg. of body weight per day. Vehicles suitable for parenteral injection may be either aqueous such as water, isotonic saline, isotonic dextrose, Ringer's solution, or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the Examples presented herein, no effort was made to recover the maximum amount of product produced or to optimize the yield of a given product. The Examples are merely illustrative of the process and of the products obtainable thereby.

The in vitro (MIC) values for erythromycylamine 11,12-carbonate against various microorganisms (clinical cultures well adapted to grow in the laboratory), determined as described above, are presented below:

| Organism* | | MIC (mcg./ml.) |
|---|---|---|
| Staphylococcus aureus | 01A005 | 0.20 |
| Staphylococcus aureus | 01A052 | 0.20 |

-continued

| Organism* | | MIC (mcg./ml.) |
|---|---|---|
| Staphylococcus aureus | 01A110R | >50 |
| Staphylococcus aureus | 01A400R | 12.5 |
| Staphylococcus epidermis | 01B037R | >50 |
| Staphylococcus epidermis | 01B111 | 0.20 |
| Staphylococcus epidermis | 01B126R | >50 |
| Streptococcus faecalis | 02A006 | 0.39 |
| Streptococcus pneumoniae | 02J012 | 0.10 |
| Streptococcus pyogenes | 02C040 | 0.78 |
| Streptococcus pyogenes | 02C203 | <.02 |
| Bacillus subtilis | 06A001 | 0.10 |
| Escherichia coli | 51A125 | 25 |
| Escherichia coli | 51A129 | 25 |
| Escherichia coli | 51A266 | 25 |
| Escherichia coli | 51A470 | 0.78 |
| Pseudomonas aeruginosa | 52A104 | >50 |
| Pseudomonas aeruginosa | 52A663 | >50 |
| Klebsiella pneumoniae | 53A009 | 50 |
| Klebsiella pneumoniae | 53A031 | 50 |
| Klebsiella oxytoca | 53D024 | >50 |
| Pasteurella multocida | 59A001 | 0.39 |
| Serratia marcescens | 63A017 | >50 |
| Neisseria sicca | 66C000 | 3.12 |
| Enterobacter aeruginosa | 67A040 | 50 |
| Enterobacter cloacea | 67B009 | >50 |
| Providentia stuarti | 77A013 | >50 |
| Providentia retgerii | 77CA025 | >50 |
| Morgani morgansus | 97A001 | >50 |
| Hemophilus influenzae | 54A036 | 3.12 |

*R = resistant to erythromycin.

EXAMPLE 1

9(S)-N-(Carbobenzoxy)Erythromycylamine

A solution of carbobenzoxy chloride (12.8 ml., 1.1 equivalent) in acetone (20 ml.) was added dropwise with stirring to a suspension of 9(S)-erythromycylamine (60 g., 81.6 mmoles), acetone (600 ml.) and pyridine (9.87 ml.) at 0°–10° C. under a nitrogen atmosphere. The reaction mixture, a yellow, gelatinous suspension, was stirred at 5°–10° C. for 45 minutes following completion of addition of the carbobenzoxy chloride. It was then poured into a mixture of water (3200 ml.)-ethyl acetate (2500 ml.) and stirred thoroughly. The pH was 6.4. The pH was adjusted to 9.8, the organic phase separated and washed successively with 500 ml. each of water and saturated sodium chloride solution and then dried over anhydrous sodium sulfate. The dried solution was evaporated under reduced pressure (water aspirator) to a pale yellow foam (72 g.). The foam was then dissolved in ether (325 ml.) and the solution stirred at room temperature for 75 minutes during which time the product crystallized. It was filtered and dried to ivory colored crystals (42.2 g.).

M.P.: 194°–195° C. (dec.).

NMR Delta$_{CDCl_3}^{TMS}$: 7.31 (5H, s); 6.36 (1H, d); 5.03 (2H, s); 3.33 (3H, s); 2.35 (6H, s).

In like manner, 9(R)-N-(carbobenzoxy)erythromycylamine is prepared from 9(R)-erythromycylamine as reactant in place of the 9(S)-epimer.

EXAMPLE 2

2'-Acetyl-9(S)-N-(Carbobenzoxy)Erythromycylamine

Acetic anhydride (2.68 ml., 0.028 mole) in ethyl acetate (10 ml.) was added dropwise with stirring to a solution of 9(S)-N-(carbobenzoxy)erythromycylamine (25.7 g., 0.028 mole) in ethyl acetate (190 ml.) under nitrogen at room temperature. The mixture was stirred for 1.5 hours following completion of addition. Thin layer chromatography (silica gel plate: 9 CHCl$_3$:1 CH$_3$OH:0.1 NH$_4$OH) of the mixture showed a small amount of unreacted 9(S)-N-(carbobenzoxy)erythromycylamine still present. Additional acetic anhydride (0.26 ml.) was added and the mixture stirred for a half hour. It was then poured into water (200 ml.) and the pH of the mixture raised to 7.0 by addition of solid sodium bicarbonate and then to 9.5 by addition of 1 N sodium hydroxide. The ethyl acetate phase was separated, washed with water (2×100 ml.), and then with saturated brine (1×100 ml.). Evaporation of the solution after drying (Na$_2$SO$_4$) gave the title product as a solid. Crystallization from hot ethyl acetate gave the product as crystals.

M.P.: 160°–166° C.

NMR delta$_{CDCl_3}^{TMS}$: 7.4 (5H, s); 6.10 (1H, d); 5.13 (2H, s); 3.41 (3H, s); 2.30 (6H, s); 2.00 (3H, s).

Thin layer chromatography (TLC) of the crystalline product in the above cited system showed only a single spot.

Replacement of acetic anhydride in the above procedure by an equivalent amount of propionic anhydride affords the corresponding 2'-propionyl-N-(carbobenzoxy)-erythromycylamine compound.

EXAMPLE 3

9(S)-N-(Carbobenzoxy)Erythromycylamine 11,12-Carbonate

A mixture of 9(S)-N-(carbobenzoxy)erythromycylamine (20 g., 23 mmoles), ethyl acetate (350 ml.), ethylene carbonate (20 g., 227 mmoles) and potassium carbonate (10 g., 72.3 mmoles) was refluxed under a nitrogen atmosphere for 3.5 hours. A second portion of ethylene carbonate (20 g.) was added and the mixture refluxed for an additional 3.5 hours. The reaction mixture was cooled to room temperature by means of a cold water bath and then poured into water (350 ml.) with stirring and the pH adjusted to 9.5 by addition of 1 N sodium hydroxide. The ethyl acetate phase was separated, washed successively with water (1×100 ml.) and saturated brine (1×100 ml.) and then dried (Na$_2$SO$_4$). Evaporation of the dried ethyl acetate solution gave the crude product as a viscous oil (29 g.) which was purified by column chromatography using 450 g. silica gel in a column 800 mm. long and 45 mm. inside diameter. The product was loaded on the column in chloroform solution and was eluted therefrom using chloroform and methanol/chloroform according to the following schedule:

| Fractions(s) | Eluant | Volume (ml.) |
|---|---|---|
| 1 | CHCl$_3$ | 2000 |
| 2–4 | 2% CH$_3$OH/CHCl$_3$ | 500 each |
| 5–17 | 4% CH$_3$OH/CHCl$_3$ | 500 each |
| 18–26 | 8% CH$_3$OH/CHCl$_3$ | 500 each |
| 27–31 | 10% CH$_3$OH/CHCl$_3$ | 500 each |

On the basis of TLC analysis of each of the above fractions using the system of Example 1, fractions 8–19 were combined and evaporated to dryness under reduced pressure (water aspirator) to give 11.6 g. of residue. Similarly, fractions 20–27 and 28–31 were combined and evaporated to dryness to give 5.6 g. and 7.5 g. of residue, respectively. In each instance the residue was an ivory colored foam.

TLC analysis of the residues using the above system showed the residue obtained from fractions 20–27 to be the desired product in substantially pure form. The residue from fractions 8-19 and 28-31 contained approximately 70% and 80%, respectively of the desired product.

NMR delta$_{CDCl_3}^{TMS}$ of fraction 20-27 product: 7.36 (5H, s); 6.36 (1H, d); 5.11 (2H, s); 3.31 (3H, s); 2.35 (6H, s); 1.48 (3H, s).

The residue (ivory colored foam) from fractions 8-19 was purified further by column chromatography using 400 g. of silica gel in a column 800 mm. long and 45 mm. wide diameter. The residue, dissolved in chloroform/5% methanol was loaded on the column and eluted with chloroform/methanol as eluting solvent according to the schedule:

| Fraction(s) | Eluant | Volume (ml.) |
| --- | --- | --- |
| 1 | 5% CH$_3$OH/CHCl$_3$ | 500 |
| 2-7 | 5% CH$_3$OH/CHCl$_3$ | 500 each |
| 8-11 | 10% CH$_3$OH/CHCl$_3$ | 500 each |
| 12-18 | 10% CH$_3$OH/CHCl$_3$ | 500 each |

Fractions 2-11 were combined and evaporated to dryness (aspirator) to give 7.29 g. of crude product estimated by TLC to contain 60% of desired product.

Fractions 12-18 were worked up in like manner to give 2.33 g. of product estimated 95% pure by TLC.

Repetition of this procedure but using 9(R)-N-(carbobenzoxy)erythromycylamine as reactant affords the epimeric 9(R)-derivative of the title compound.

EXAMPLE 4

2'-Acetyl-9(S)-N-(Carbobenzoxy)-Erythromycylamine 11,12-Carbonate

A solution of acetic anhydride (6.82 ml., 72.2 mmoles) in ethyl acetate (20 ml.) is added dropwise over a three minute period to a stirring solution of 9(S)-N-(carbobenzoxy)erythromycylamine 11,12-carbonate (60 g., 65.7 mmoles; estimated 98% pure in the TLC system of Example 1) at room temperature. An additional 0.682 ml. of acetic anhydride was added after 1.75 hours of stirring and the stirring continued for an additional 15 minutes. The reaction mixture was then poured into water (500 ml.) and worked-up according to the work-up procedure of Example 2. The white foam obtained (58.2 g.) gave the following NMR analysis:

NMR delta$_{CDCl_3}^{TMS}$: 7.40 (5H, s); 5.58 (1H, d); 5.16 (2H, s); 3.40 (3H, s); 2.33 (6H, s); 2.00 (3H, s); 1.50 (3H, s).

In like manner, 2'-acetyl-9(R)-N-(carbobenzoxy)-erythromycylamine 11,12-carbonate is prepared from 9(R)-N-(carbobenzoxy)erythromycylamine 11,12-carbonate.

EXAMPLE 5

2'-Acetyl-9(S)-N-(Carbobenzoxy)-Erythromycylamine 11,12-Carbonate

A mixture of 2'-acetyl-9(S)-N-(carbobenzoxy)-erythromycylamine (300 mg., 0.329 mmole), ethylene carbonate (300 mg., 3.0 mmoles), potassium carbonate (150 mg., 1.09 mmoles) and ethyl acetate (5 ml.) was refluxed under a nitrogen atmosphere for 20 hours. The reaction mixture was then poured into a stirring mixture of ethyl acetate-water (50 ml. of each) and the pH adjusted to 9.5 by addition of sodium hydroxide. The ethyl acetate phase was separated, and washed first with water (25 ml.), then with saturated brine (25 ml.), and dried (Na$_2$SO$_4$). Evaporation of the dried ethyl acetate solution to dryness gave the product as a white foam (305 mg.).

EXAMPLE 6

2'-Propionyl-9(S)-N-(Carbobenzoxy)-Erythromycylamine 11,12-Carbonate

To a solution of 9(S)-N-(carbobenzoxy)erythromycylamine 11,12-carbonate (3.55 g., 3.68 mmoles) in methylene chloride (35 ml.) was added propionic anhydride (0.519 ml., 4.04 mmoles). The mixture was stirred for three hours at room temperature and was then poured, with stirring, into a mixture of water-methylene chloride (20 ml. of each) and the pH adjusted to 10. The organic phase was separated, washed with water (2×25 ml.), then with saturated brine (1×25 ml.) and dried (Na$_2$SO$_4$). Evaporation to dryness under reduced pressure (aspirator) gave 3.48 g. of the title product as a white foam.

NMR delta$_{CDCl_3}^{TMS}$: 1.46 (3H, s); 2.26 (6H, s); 3.33 (3H, s); 5.10 (2H, s); 7.30 (5H, s).

Repetition of this procedure but substituting 9(R)-N-(carbobenzoxy)erythromycylamine 11,12-carbonate for its 9(S)-epimer affords 2'-propionyl-9(R)-N-(carbobenzoxy)erythromycylamine 11,12-carbonate.

EXAMPLE 7

2'-(3-Carbethoxypropionyl)-9(S)-N-(Carbobenzoxy)Erythromycylamine 11,12-Carbonate Ethyl succinyl chloride (0.575 ml., 4.04 mmoles) was added with stirring to a solution of 9(S)-N-(carbobenzoxy)erythromycylamine 11,12-carbonate (3.55 g., 3.68 mmoles) in methylene chloride (35 ml.) at room temperature. After three hours of stirring an additional 0.575 ml. of ethyl succinyl chloride was added and stirring continued for 1.5 hours. A third quantity of ethyl succinyl chloride (0.288 ml.) was then added and, after stirring for 40 minutes, the mixture was poured into a mixture of water-methylene chloride (20 ml. of each). The mixture was worked-up according to the procedure of Example 6 to give 4.08 g. of a gold colored foam.

NMR delta$_{CDCl_3}^{TMS}$: 1.53 (3H, s); 2.25 (6H, s); 2.61 (4H, s); 3.35 (3H, s); 5.11 (2H, s); 7.33 (5H, s).

2'-Carbethoxypropionyl-9(R)-N-(carbobenzoxy)-erythromycyclamine 11,12-carbonate is prepared by the above procedure using 9(R)-N-(carbobenzoxy)erythromycylamine 11,12-carbonate as reactant.

EXAMPLE 8

2'-Acetyl-9(S)-Erythromycylamine 11,12-Carbonate

Palladium-on-charcoal (1.0 g. of 10%) was added to 2'-acetyl-9(S)-N-(carbobenzoxy)erythromycylamine 11,12-carbonate (3.21 g., 3.42 mmoles) in isopropanol (50 ml.) and the mixture hydrogenated in a Parr shaker at room temperature and 3.52 kg./sq. cm. (50 psi) for 5 hours. The mixture was filtered through diatomaceous earth and then evaporated to dryness under reduced pressure (aspirator). The resulting foam was slurried in ether (25 ml.) for a half hour and the white crystalline product filtered and dried at 56° C. under high vacuum (0.5 mm. Hg.) for 4 hours. Yield=1.6 g.

M.P.: 134°-138° C. (dec.).

NMR delta$_{CDCl_3}^{TMS}$: 1.50 (3H, s); 2.06 (3H, s); 2.30 (6H, s); 3.36 (3H, s).

The epimeric 9(R)-derivative is prepared in like manner from 2'-acetyl-9(R)-erythromycylamine 11,12-carbonate.

EXAMPLE 9

2'-Propionyl-9(S)-Erythromycylamine 11,12-Carbonate

Hydrogenation of 2'-propionyl-9(S)-N-(carbobenzoxy)-erythromycylamine 11,12-carbonate (3.37 g., 3.54 mmoles) in isopropanol solution (50 ml.) using palladium-on-charcoal (1.0 g. of 10%) in a Parr shaker at room temperature and 3.52 kg./sq. cm. (50 psi) hydrogen pressure for 4.75 hours, followed by filtration and evaporation (roto-vac, aspirator) gave 2.8 g. of a white foam. The foam was stirred in isopropyl ether (50 ml.) for one hour during which time it became crystalline. Filtration and drying of the product at 56° C. for 4 hours under high vacuum (0.5 mm. Hg) gave 1.1 g. of the title product as white crystals.

M.P.: 141°–149° C. (dec.).

NMR delta$_{CDCl_3}^{TMS}$: 1.50 (3H, s); 2.31 (6H, s); 3.35 (3H, s).

EXAMPLE 10

2'-(3-Carbethoxypropionyl)-9(S)-Erythromycylamine 11,12-Carbonate

Catalytic hydrogenation of 2'-(3-carbethoxypropionyl)-9(S)-N-(carbobenzoxy)erythromycylamine 11,12-carbonate (3.98 g., 3.57 mmoles) in isopropanol (50 ml.) in the presence of palladium-on-charcoal (1.0 g. of 10%) at room temperature and 3.52 kg./sq. cm. (50 psi) for 4.5 hours followed by filtration and evaporation of the filtrate gave 2.51 g. of a white foam. The foam was slurried in ether (15 ml.) for about one hour and the crystalline product filtered and dried in vacuo (0.5 mm. Hg.) at 56° C. for 5 hours.

M.P.: 130°–133° C. (dec.).

NMR delta$_{CDCl_3}^{TMS}$: 1.50 (3H, s); 2.33 (6H, s); 2.66 (4H, s); 3.35 (3H, s).

Similarly, the 9(R)-epimer of the title compound is prepared from 2'-(3-carbethoxypropionyl)-9(R)-N-(carbobenzoxy)erythromycylamine 11,12-carbonate.

EXAMPLE 11

9(S)-Erythromycin 11,12-Carbonate

Palladium-on-charcoal (1.0 g. of 10%), methanol (75 ml.) and 9(S)-N-(carbobenzoxy)erythromycylamine 11,12-carbonate were introduced into a Parr shaker and hydrogenated at 3.52 kg./sq. cm. at room temperature for 1-5 hours. The reaction mixture was removed from the shaker, filtered and evaporated to dryness under reduced pressure (water aspirator) to give a white foam (1.57 g.). The foam was dissolved in a mixture of chloroform (30 ml.)/water (30 ml.) with vigorous stirring. The pH was adjusted to 10.3 by addition of 1 N sodium hydroxide, the chloroform phase separated and dried (Na$_2$SO$_4$). Evaporation of the dried chloroform solution under reduced pressure (water aspirator) gave the product as a white, partially crystalline solid. The solid was crystallized from hot chloroform (15 ml.)/hexane (30 ml.) as white crystals which were recovered by filtration and dried under high vacuum at 60° C. for four hours. Yield=850 mg.

M.P.: softened at 125° C. and melted to a gum at 128°–131° C.

NMR delta$_{CDCl_3}^{TMS}$: 3.36 (3H, s); 2.40 (6H, s); 1.51 (3H, s).

By means of the above procedure, 9(R)-erythromycylamine 11,12-carbonate is prepared from 9(R)-N-(carbobenzoxy)-erythromycylamine 11,12-carbonate.

EXAMPLE 12

9-(S)-N-(Carbobenzoxy)Erythromycylamine 11,12-Carbonate

Carbobenzoxy chloride (10.3 ml., 72.3 mmoles) in acetone (40 ml.) was added dropwise over a fifteen minute period to a rapidly stirred mixture of 9(S)-erythromycylamine 11,12-carbonate (50 g., 65.7 mmoles) and pyridine (7.94 ml., 98.5 mmoles) in acetone (1500 ml.) at −8° C. The temperature rose to −4° C. during the addition. The mixture was stirred for a half hour following completion of addition and was then evaporated (water aspirator) to dryness to give an oily yellow suspension. The suspension was dissolved in ethyl acetate (500 ml.)/water (500 ml.), thoroughly stirred and the pH adjusted to 10.1. The ethyl acetate phase was separated, washed with saturated brine (1×100 ml.) and then dried (Na$_2$SO$_4$). Evaporation of the dried ethyl acetate solution (water aspirator) gave an ivory foam which was dried further under high vacuum overnight at room temperature. Yield=60.1 g.

The NMR of the product is in agreement with that of the product of Example 3.

EXAMPLE 13

9(S)-Erythromycylamine 11,12-Carbonate (directly from 9(S)-erythromycylamine)

A mixture of 9(S)-erythromycylamine (150 g., 0.204 mole), ethylene carbonate (400 g., 4.51 mmoles), potassium carbonate (150 g., 1.08 moles) and ethyl acetate (1500 ml.) was refluxed for 40 hours and then cooled to room temperature. The golden colored reaction mixture was poured into 1500 ml. of water, stirred rapidly and the pH of the mixture raised to 10.6 by addition of 1 N sodium hydroxide. The ethyl acetate phase was separated, added to rapidly stirring volume (1500 ml.) of water and the pH adjusted to 2.1 by addition of 1 N hydrochloric acid.

The ethyl acetate phase was separated and the aqueous phase extracted with ethyl acetate (500 ml.). The aqueous phase was separated, added to a rapidly stirring solution of ethyl acetate (1500 ml.) and the pH adjusted to 10.3 with 1 N sodium hydroxide. The ethyl acetate phase was separated, washed with saturated brine (1×500 ml.) and dried (Na$_2$SO$_4$). Evaporation of the dry ethyl acetate solution to dryness (aspirator) gave a gummy solid which was then slurried in ether (200 ml.) to produce white crystals. The crystals were separated by filtration, then dried. Yield=54.9 g.

M.P.: softens at 127° C. and melted to a clear gel at 128°–131° C.

NMR delta$_{CDCl_3}^{TMS}$: 3.36 (3H, s); 2.40 (6H, s); 1.51 (3H, s).

MS—m/e: 602, 558, 444, 400, 159, 158.

Repetition of the above procedure but substituting 9(R)-erythromycylamine for its 9(S)-epimer affords 9(R)-erythromycylamine 11,12-carbonate.

EXAMPLE 14

9(S)-Erythromycylamine 11,12-Carbonate

A mixture of 9(S)-erythromycylamine (2.5 g., 3.4 mmoles), ethylene carbonate (2.5 g., 28.4 mmoles), potassium carbonate (1.25 g., 9.04 mmoles) and toluene (25 ml.) was refluxed for 2.75 hours and then cooled to room temperature. It was poured with stirring into a mixture of ethyl acetate/water (25 ml. of each) and the pH adjusted to 10.4. The ethyl acetate phase was separated, combined with fresh water (25 ml.) and, with stirring, the pH adjusted to 2.1 by addition of 1 N hydrochloric acid. The phases were separated and the aqueous phase extracted with ethyl acetate (25 ml.). The aqueous phase was then added to fresh ethyl acetate (25 ml.), the mixture stirred and adjusted to pH 9.8 by addition of 1 N sodium hydroxide. The ethyl acetate phase was separated, dried ($Na_2SO_4$) and evaporated (aspirator) to a white foam (2.79 g.).

The foam was dissolved in ethyl acetate (20 ml.) in a glass beaker and crystallization achieved by scratching its walls with a glass rod. After stirring for a half hour at room temperature, the crystals were filtered off and dried under high vacuum. Yield=611 mg. It was identical to the product of Example 13.

Additional product was recovered by evaporating the mother liquor to dryness and trituration of the resulting white foam with ether to produce white crystals. Yield=274 mg. TLC in the system $CHCl_3$: methanol:$NH_4OH$ (6:1:0.1) showed it to contain only a trace of impurity.

EXAMPLE 15

9(S)-Erythromycylamine 11,12-Carbonate Phosphate

Phosphoric acid (3.59 ml. of 85%) was added to a rapidly stirring suspension of 9(S)-erythromycylamine 11,12-carbonate (20 g., 26.3 mmoles) in isopropanol (400 ml.) at room temperature. The mixture was stirred for one hour and the salt recovered by filtration. It was washed with isopropanol and dried overnight at room temperature in a vacuum dessicator and then at 50° C. for another 12 hours. Yield=21.3 g. of white crystals. M.P.: 153°–162° C.

NMR $delta_{CDCl_3}^{TMS}$: 3.36 (3H, s); 2.78 (6H, s); 1.28 (3H, s).

In like manner, the following acid addition salts of 9(S)- and 9(R)-erythromycylamine 11,12-carbonate, and of 2'-acetyl, 2'-propionyl- and 2'-carbethoxypropionyl-9(S)- and 9(R)-erythromycylamine 11,12-carbonate are prepared: hydrochloride, sulfate, nitrate, succinate, maleate, aspartate, formate, acetate, propionate, butyrate, citrate, glycolate, malate, tartrate, gluconate, fumarate, pamoate, mandelate, lactate, p-toluenesulfonate, mesylate and oxalate.

EXAMPLE 16

9(S)-Erythromycylamine 11,12-Carbonate

Solvolysis of 2'-acetyl-9(S)-erythromycylamine 11,12-carbonate is accomplished by stirring 0.5 g. of said compound in methanol (20 ml.) at room temperature for 24 hours followed by removal of the solvent under reduced pressure (aspirator).

Similarly, the corresponding 2'-propionyl and 2'-carbethoxypropionyl derivatives, and the N-carbobenzoxy derivatives of said compounds are solvolyzed to remove the alkanoyl group.

I claim:

1. A compound of formula I

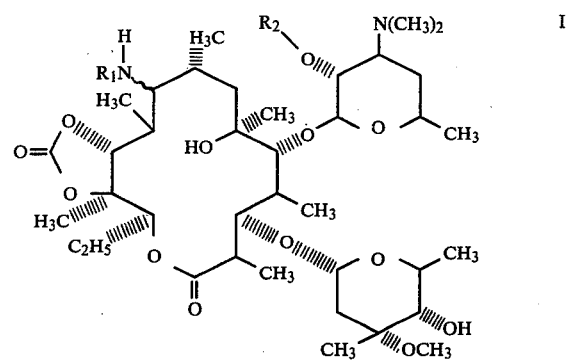

wherein $R_1$ is hydrogen or N-carbobenzoxy; and $R_2$ is hydrogen, acetyl, propionyl or 3-carbethoxypropionyl; or the pharmaceutically acceptable acid addition salts of those compounds wherein $R_1$ is hydrogen.

2. A compound according to claim 1, formula I, wherein $R_1$ is hydrogen and $R_1NH$ has the 9(S)-configuration.

3. The compound according to claim 2 wherein $R_2$ is hydrogen.

4. The compound according to claim 2 wherein $R_2$ is acetyl.

5. The compound according to claim 2 wherein $R_2$ is propionyl.

6. The compound according to claim 2 wherein $R_2$ is 3-carbethoxypropionyl.

7. A compound according to claim 1, formula I, wherein $R_1$ is carbobenzoxy.

8. The compound according to claim 7 wherein $R_2$ is hydrogen.

9. The compound according to claim 7 wherein $R_2$ is acetyl.

10. The compound according to claim 7 wherein $R_2$ is 3-carbethoxypropionyl.

11. The compound according to claim 7 wherein $R_2$ is propionyl.

* * * * *